(12) United States Patent
Choi et al.

(10) Patent No.: US 11,125,734 B2
(45) Date of Patent: Sep. 21, 2021

(54) GAS SENSOR PACKAGE

(71) Applicant: Samsung Electronics Co., Ltd., Suwon-si (KR)

(72) Inventors: Inho Choi, Seoul (KR); Minjin Kim, Seoul (KR); Sungwoo Park, Anyang-si (KR); Youngdoo Jung, Suwon-si (KR); Eunhee Jung, Hwaseong-si (KR); Sungeun Jo, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 165 days.

(21) Appl. No.: 16/109,758

(22) Filed: Aug. 23, 2018

(65) Prior Publication Data

US 2019/0204281 A1 Jul. 4, 2019

(30) Foreign Application Priority Data

Jan. 2, 2018 (KR) .................. 10-2018-0000190

(51) Int. Cl.
*G01N 33/00* (2006.01)
*H01L 23/31* (2006.01)
(Continued)

(52) U.S. Cl.
CPC ....... *G01N 33/006* (2013.01); *G01N 33/0031* (2013.01); *H01L 23/10* (2013.01);
(Continued)

(58) Field of Classification Search
CPC . H01L 2224/73265; H01L 2224/32145; H01L 2224/48227; H01L 2924/00014; H01L 2924/00; H01L 2924/00012; H01L 2224/32225; H01L 2224/48247; H01L 2224/131; H01L 2224/32245; H01L 2224/48091; H01L 2224/48145; H01L 2924/15311; H01L 2224/45099; H01L 2924/014; H01L 2224/0401; H01L 2224/04042; H01L 2224/16227; H01L 2224/16245; H01L 2224/48106;
(Continued)

(56) References Cited

U.S. PATENT DOCUMENTS 4,457,161 A * 7/1984 Iwanaga ............ G01N 33/0031
340/634
6,140,144 A * 10/2000 Najafi .................. B81C 1/00269
438/106
(Continued)

FOREIGN PATENT DOCUMENTS

JP 2010008371 A * 1/2010
JP 2012-047451 A 3/2012
JP 4892521 B2 3/2012

*Primary Examiner* — John Fitzgerald
*Assistant Examiner* — Truong D Phan
(74) *Attorney, Agent, or Firm* — Muir Patent Law, PLLC

(57) ABSTRACT

Disclosed is a gas sensor package. The gas sensor package comprises a package substrate, a controller on the package substrate, a plurality of gas sensors on the controller, and a lid on the package substrate and the lid comprising a hole extending between a first surface and a second surface of the lid, the first surface of the lid facing away the package substrate and the second surface of the lid facing toward the package substrate. The gas sensors sense different types of gases.

18 Claims, 12 Drawing Sheets

(51) Int. Cl.
  *H01L 23/00*    (2006.01)
  *H01L 23/498*   (2006.01)
  *H01L 23/10*    (2006.01)
  *H01L 23/552*   (2006.01)

(52) U.S. Cl.
  CPC .... *H01L 23/3121* (2013.01); *H01L 23/49838* (2013.01); *H01L 23/564* (2013.01); *H01L 24/48* (2013.01); *H01L 24/49* (2013.01); *H01L 23/552* (2013.01); *H01L 2224/48091* (2013.01); *H01L 2224/48106* (2013.01); *H01L 2224/48145* (2013.01); *H01L 2224/48227* (2013.01); *H01L 2224/49109* (2013.01); *H01L 2924/00014* (2013.01); *H01L 2924/3025* (2013.01)

(58) Field of Classification Search
  CPC . H01L 2224/49109; H01L 2224/49171; H01L 2224/49174; H01L 23/10; H01L 23/3121; H01L 23/49838; H01L 23/552; H01L 23/564; H01L 24/13; H01L 24/16; H01L 24/48; H01L 24/49; H01L 24/73; H01L 2924/15313; H01L 2924/16151; H01L 2924/16251; H01L 2924/3025; H01L 2224/48229; H01L 2924/01079; H01L 23/293; H01L 2924/01078; G01N 33/0031; G01N 33/006; G01N 27/4077; G01N 27/12; G01N 27/407; G01N 27/414; G01N 33/005; G01N 27/16; G01N 7/06; H05K 7/142; H05K 3/301; G06F 1/184; G01M 15/102
  USPC .................. 73/31.05, 31.06, 23.31; 361/807; 422/94; 257/788
  See application file for complete search history.

(56) References Cited

U.S. PATENT DOCUMENTS

| | | | |
|---|---|---|---|
| 6,586,824 B1 * | 7/2003 | Glenn | H01L 23/3128 257/239 |
| 7,468,556 B2 * | 12/2008 | Logan | B81C 1/0023 257/723 |
| 7,479,255 B2 | 1/2009 | Otani et al. | |
| 7,712,349 B2 | 5/2010 | Katsuda et al. | |
| 7,906,859 B2 | 3/2011 | Yoshioka et al. | |
| 7,936,062 B2 * | 5/2011 | Humpston | B81C 1/00269 257/680 |
| 8,852,513 B1 | 10/2014 | Speer et al. | |
| 8,900,931 B2 * | 12/2014 | Liang | H01L 23/315 438/126 |
| 9,105,479 B2 | 8/2015 | Besling et al. | |
| 9,324,586 B2 * | 4/2016 | Theuss | H01L 21/565 |
| 9,374,643 B2 * | 6/2016 | Szczech | H04R 19/005 |
| 9,778,238 B2 | 10/2017 | van der Avoort et al. | |
| 9,794,661 B2 * | 10/2017 | Watson | H04R 1/023 |
| 9,970,911 B2 * | 5/2018 | Paik | G01N 33/0042 |
| 10,126,258 B2 * | 11/2018 | Paik | H01L 23/49816 |
| 10,527,572 B2 * | 1/2020 | Matsumoto | G01N 27/16 |
| 2003/0160021 A1 * | 8/2003 | Platt | B81C 1/00269 216/2 |
| 2004/0003664 A1 * | 1/2004 | Ishikawa | G01N 29/223 73/644 |
| 2004/0188250 A1 * | 9/2004 | Sakai | G01N 33/0037 204/412 |
| 2004/0188622 A1 * | 9/2004 | Yokura | G01N 21/3504 250/343 |
| 2005/0116174 A1 * | 6/2005 | Berdermann | G01T 1/26 250/370.01 |
| 2006/0032745 A1 * | 2/2006 | Davies | G01N 27/16 204/431 |
| 2006/0243029 A1 * | 11/2006 | Lange | G01N 33/0016 73/31.05 |
| 2007/0107493 A1 * | 5/2007 | Katsuda | G01N 33/0009 73/23.31 |
| 2015/0075258 A1 * | 3/2015 | Paik | G01N 27/041 73/31.06 |
| 2015/0177028 A1 | 6/2015 | Lee et al. | |
| 2015/0177171 A1 * | 6/2015 | Kim | G01N 27/128 73/31.05 |
| 2015/0216068 A1 | 7/2015 | Kim et al. | |
| 2015/0226688 A1 * | 8/2015 | Watanabe | G01N 27/18 73/31.05 |
| 2015/0285772 A1 * | 10/2015 | Park | G01N 33/0031 73/31.05 |
| 2016/0137491 A1 * | 5/2016 | Su | B81B 7/02 257/418 |
| 2017/0284951 A1 * | 10/2017 | Pindl | G01N 33/0036 |
| 2017/0316995 A1 * | 11/2017 | Hwang | G01N 27/123 |
| 2018/0003685 A1 * | 1/2018 | Cummings | G01N 27/04 |
| 2018/0136064 A1 * | 5/2018 | Leuschner | G01N 33/0027 |
| 2018/0231481 A1 * | 8/2018 | Tsai | G01N 27/04 |
| 2018/0273376 A1 * | 9/2018 | Feyh | H01L 23/28 |
| 2019/0170675 A1 * | 6/2019 | Liu | G01N 27/16 |
| 2019/0212312 A1 * | 7/2019 | Kim | H01L 23/49805 |
| 2019/0250135 A1 * | 8/2019 | Andersson | G01N 27/125 |

* cited by examiner

GAS SENSOR PACKAGE

CROSS-REFERENCE TO RELATED APPLICATIONS

This U.S. nonprovisional application claims priority under 35 U.S.C. § 119 to Korean Patent Application No. 10-2018-0000190 filed on Jan. 2, 2018, in the Korean Intellectual Property Office, the entire contents of which are hereby incorporated by reference.

BACKGROUND

Example embodiments according to the inventive concepts relate to a gas sensor package.

In general, a gas sensor measures the amount of an analysis target gas by using characteristics of changes in electrical conductivity or electrical resistance in accordance with adsorption of gas molecules. The gas sensor may be manufactured using metal oxide semiconductor, solid electrolyte material, or other organic materials.

Air quality generally influences human health. As indoor spaces have been further enclosed and use of building materials containing chemicals has increased, air pollution has become social issues. The gas sensor may be beneficial to achieve improved accuracy. In addition, researches are being conducted to apply the gas sensor to cellular phones or wearable devices.

SUMMARY

Some example embodiments of inventive concepts provide a gas sensor package having improved sensing accuracy and enhanced durability.

According to exemplary embodiments of inventive concepts, a gas sensor package may comprise: a package substrate; a controller on the package substrate; a plurality of gas sensors laterally spaced apart from each other on an upper surface of the controller; a lid on the package substrate and positioned over the plurality of gas sensors, the lid having a hole extending between a first surface and a second surface of the lid, the first surface of the lid facing away the package substrate and the second surface of the lid facing toward the package substrate; and a protection film covering the hole of the lid, wherein the gas sensors are configured to sense different types of gases.

According to exemplary embodiments of inventive concepts, a gas sensor package may comprise: a package substrate; a first gas sensor on the package substrate, the first gas sensor comprising a first sensing part and a first bonding pad laterally spaced apart from each other on a top surface of the first gas sensor; a second gas sensor on the package substrate, the second gas sensor comprising a second sensing part and a second bonding pad laterally spaced apart from each other on a top surface of the second gas sensor; a molding layer on the package substrate, the molding layer covering the first bonding pad and the second bonding pad; and a protection film on the molding layer, the protection film being spaced apart from the top surface of the first gas sensor and the top surface of the second gas sensor, wherein the molding layer exposes the first sensing part and the second sensing part.

DETAILED DESCRIPTION OF EMBODIMENTS

Figure 1A:
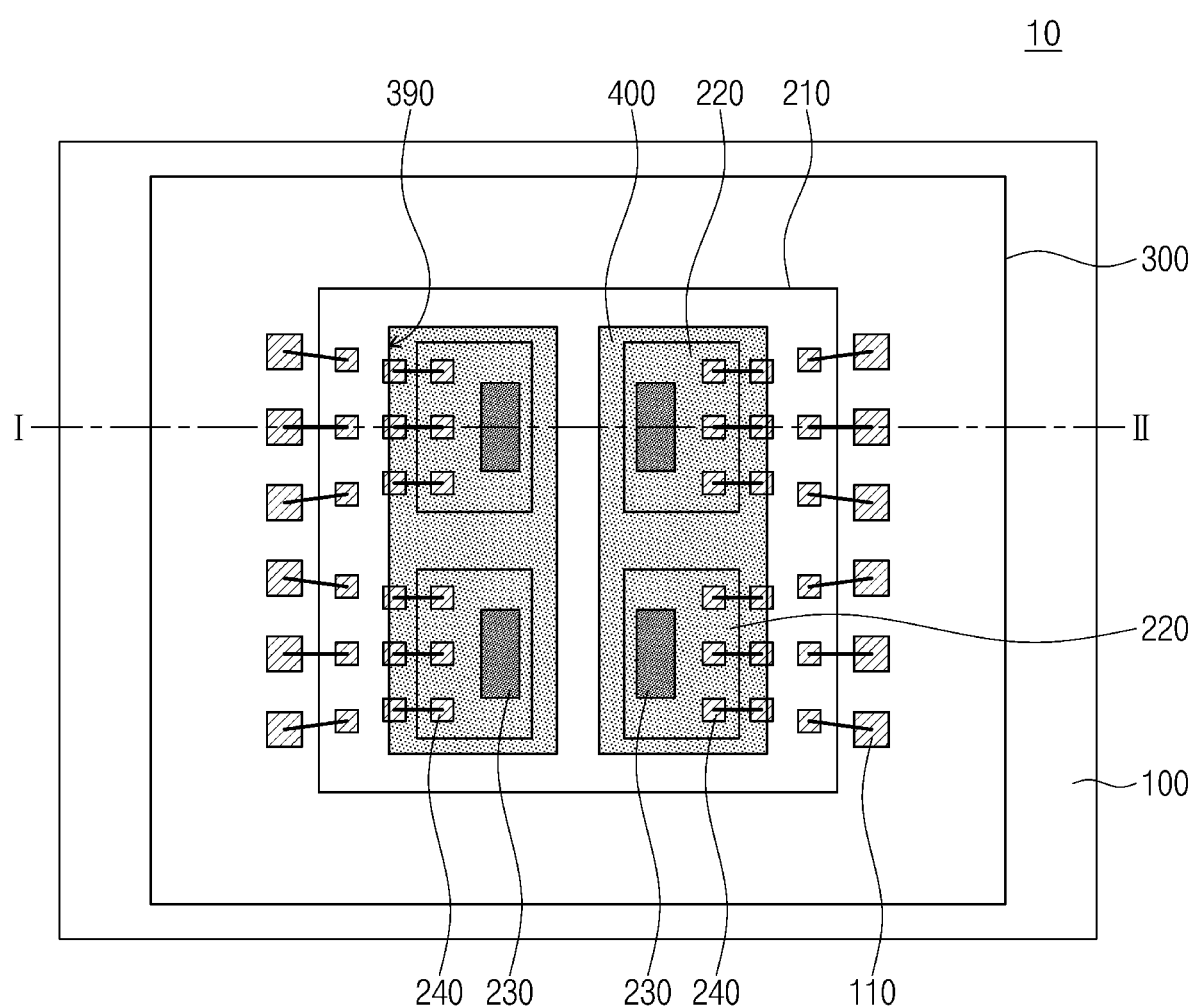
FIG. 1A illustrates a plan view showing a gas sensor package according to exemplary embodiments.

It will be described exemplary embodiments of inventive concepts with reference to the accompanying drawings. Like reference numerals may indicate like components throughout the description.

It will now be discussed a gas sensor package according to exemplary embodiments of the inventive concepts.

Figure 1B:
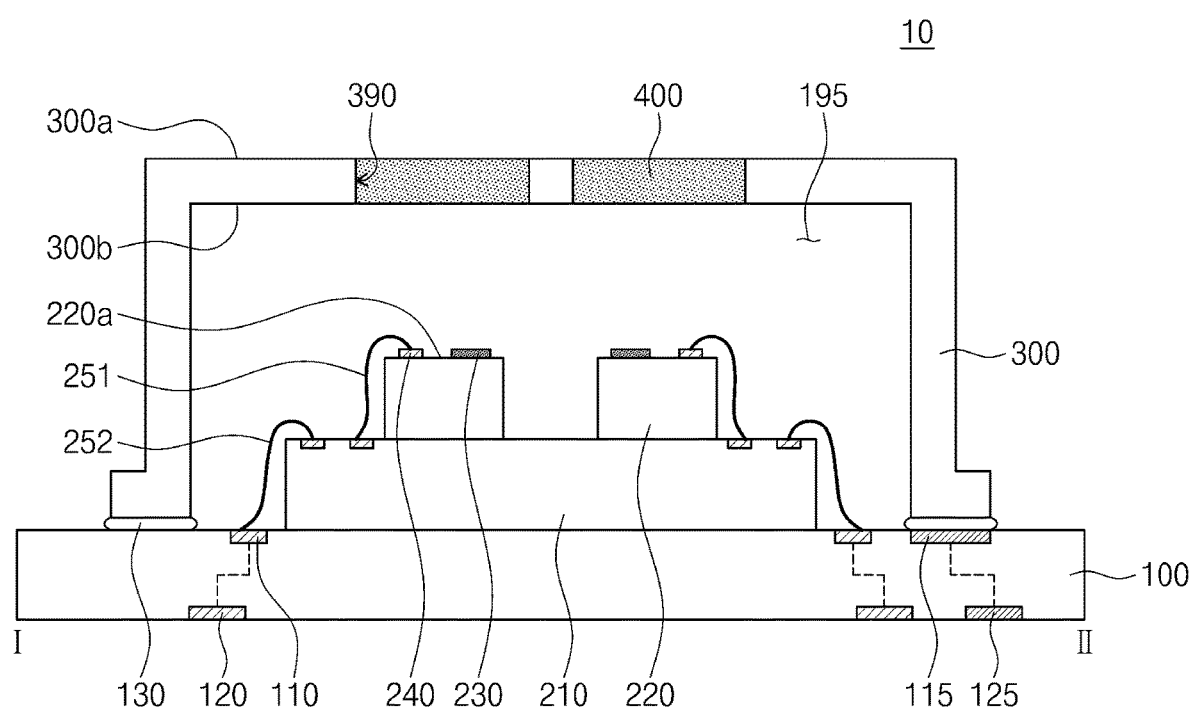
FIG. 1B illustrates a cross-sectional view taken along line I-II of FIG. 1A.

FIG. 1A illustrates a plan view showing a gas sensor package according to exemplary embodiments. FIG. 1B illustrates a cross-sectional view taken along line I-II of FIG. 1A.

Referring to FIGS. 1A and 1B, a gas sensor package 10 may include a package substrate 100, a control device 210 (e.g., control circuitry), a sensing device 220 (e.g., sending circuitry), a first bonding wire 251, a lid 300, and a protection film 400. The gas sensor package 10 may sense gases. The package substrate 100 may include, for example, a printed circuit board (PCB) or a lead frame. An upper conductive pad 110 and a lower conductive pad 120 may be respectively disposed on top and bottom surfaces of the package substrate 100. A solder ball (not shown) may further be provided on the lower conductive pad 120. The lower conductive pad 120 may be coupled to an external device external to the gas sensor package 10. The lower conductive pad 120 may be electrically connected through an internal wiring line to the upper conductive pad 110. An upper ground pad 115 and a lower ground pad 125 may be respectively disposed on the top and bottom surfaces of the package substrate 100 at an edge portion of the package substrate 100, but the disclosure is not limited thereto. A solder ball (not shown) may further be provided on the lower ground pad 125. The lower ground pad 125 may be supplied with a ground voltage. The lower ground pad 125 may be electrically connected through an internal wiring line to the upper ground pad 115. In figures, a dotted line schematically indicates an internal wiring line within the package substrate 100. In this description, the phrase "electrically connected/coupled" may include a direct connection/coupling or an indirect connection/coupling through other conductive component(s). The upper conductive pad 110, the lower conductive pad 120, the upper ground pad 115, and the lower ground pad 125 may include metal such as aluminum or copper.

The various pads of a device described herein may be conductive terminals connected to internal wiring of the device, and may transmit signals and/or supply voltages between an internal wiring and/or internal circuit of the device and an external source. For example, chip pads of a semiconductor chip may electrically connect to and transmit supply voltages and/or signals between an integrated circuit of the semiconductor chip and a device to which the semiconductor chip is connected. The various pads may be provided on or near an external surface of the device and may generally have a planar surface area (often larger than a corresponding surface area of the internal wiring to which they are connected) to promote connection to a further terminal, such as a bump or solder ball, and/or an external wiring.

The control device 210 may be mounted on the package substrate 100. A second bonding wire 252 may be coupled both to the upper conductive pad 110 and to a chip pad of the control device 210. The control device 210 may be electrically connected through the second bonding wire 252 to the package substrate 100. Alternatively, the control device 210 may mounted on the package substrate 100 in a flip-chip manner. In this case, the control device 210 may be electrically connected to the package substrate 100 through a bump or solder (not shown).

Those skilled in the art will appreciate that the control device 210 and the sensing device 220 may be physically implemented by electronic circuits such as logic circuits, discrete components, microprocessors, hard-wired circuits, wiring connections, and the like, which may be formed using semiconductor-based fabrication techniques or other manufacturing technologies. According to example embodiments, the control device 210 may include a semiconductor chip. The control device 210 may include therein a plurality of integrated circuits such as CMOS transistors. The sensing device 220 may include a gas sensor chip for sensing gases. The control device 210 may control the sensing device 220. The control device 210 may be referred to as controller.

As used herein, and unless indicated otherwise, items described as being "electrically connected" are configured such that an electrical signal can be passed from one item to the other. Therefore, a passive electrically conductive component (e.g., a wire, pad, internal electrical line, etc.) physically connected to a passive electrically insulative component (e.g., a prepreg layer of a printed circuit board, an electrically insulative adhesive connecting two devices, an electrically insulative underfill or mold layer, etc.) that does not permit electric current to pass therethrough is not electrically connected to that component.

The sensing device 220 may be stacked on a top surface of the control device 210. The sensing device 220 may include a sensing part 230 and a bonding pad 240 that are disposed on a top surface 220a of the sensing device 220. The sensing part 230 and the boding pad 240 may be disposed on the top surface 220a of the sensing device 220 spaced apart from each other by a predetermined distance in a direction parallel to an upper surface package substrate 100. For example, the sensing part 230 and the boding pad 240 may be disposed on opposing edges of the top surface 220a of the sensing device 220. The sensing part 230 may include a sensing pad to which an analysis target gas is adsorbed. The sensing device 220 may be provided in plural and may be stacked on the top surface of the control device 210 spaced apart from each other by a predetermined distance in a direction parallel to an upper surface package substrate 100. For example, one of the plurality of sensing devices 220 may be disposed on one edge of the top surface of the control device 210 and the other one of the plurality of sensing devices 220 may be disposed on the other edge of the top surface of the control device 210 in a direction parallel to an upper surface package substrate 100.

According to example embodiments, a gas adsorbed to the sensing part 230 may depend on a material composition of the sensing part 230. For example, one of the plurality of sensing devices 220 may have a different material composition from that of other of the plurality of sensing devices 220. The material composition of the sensing part 230 may mean a material composition of the sensing pad included in the sensing part 230. A gas adsorbed to one of the sensing parts 230 may be of different type from a gas adsorbed to other of the sensing parts 230. The sensing devices 220 may accordingly sense different types of gases from each other. For example, one of the sensing devices 220 may sense an amine gas, and other of the sensing devices 220 may sense a toluene gas. The gas sensor package 10 may thus quantitatively or qualitatively analyze various types of gases. The number of the sensing devices 220 may depend on types of analysis target gases. The bonding pad 240 may be laterally spaced apart from the sensing part 230.

The first bonding wire 251 may be provided on the top surface 220a of each of the sensing devices 220. The first bonding wire 251 may be coupled both to the bonding pad 240 and a chip pad of the control device 210. Each of the sensing devices 220 may be electrically connected through the first bonding wire 251 to the control device 210. In this description, the phrase "electrically connected to the control device 210/sensing devices 220" may mean "electrically connected to integrated circuits of the control device 210/sensing devices 220."

The lid 300 may be disposed on the package substrate 100. The lid 300 may include metal, a plastic, and a polymer. The lid 300 may protect the control device 210 and the sensing devices 220 from external stresses. The external stresses may be or include, for example, physical impacts or impurities. The impurities may include moisture and/or dust. A cavity 195 may be defined by the package substrate 100, the lid 300, and the protection film 400. For example, the cavity 195 may be a space surrounded by the package substrate 100, the lid 300, and the protection film 400. The cavity 195 may be occupied by gases. The gases may include an analysis target gas.

The lid 300 may include a hole 390. The lid 300 may have a first surface 300a and a second surface 300b. The second surface 300b of the lid 300 may be opposite to the first surface 300a of the lid 300. The second surface 300b of the lid 300 may face toward the package substrate 100 and the first surface 300a of the lid 300 may face away from the package substrate 100. The hole 390 may penetrate the first and second surfaces 300a and 300b of the lid 300. For example, the hole 390 may extend between the first and second surfaces 300a and 300b of the lid 300. A gas may flow through the hole 390 into the cavity 195. At least two holes 390 may be provided. An external gas may be introduced into the cavity 195 through one of the holes 390. A gas within the cavity 195 may flow out through other of the holes 390. A gas may then satisfactorily flow between the cavity 195 and an external space external to the gas sensor package 10. Differently from that shown, at least one of the holes 390 may be provided on a sidewall of the lid 300. The holes 390 may be variously changed in number and planar shape.

The protection film 400 may reside in and block the holes 390. The protection film 400 may overlap the holes 390 when viewed in plan as illustrated in FIG. 1A. The cavity 195 may be provided among the protection film 400 and the sensing devices 220. The protection film 400 may include a waterproof film through which a gas flows. An external gas may be introduced through the protection film 400 into the cavity 195. The sensing devices 220 may sense one or more gases within the cavity 195. The sensing devices 220 may be referred to as gas sensors. External impurities may have difficulty in passing through the protection film 400. The impurities may include moisture and/or dust. The occurrence of sensing noise due to the impurities may thus be prevented to improve sensing accuracy of the sensing devices 220. It may be possible to prevent or reduce impurity-induced damages to the sensing devices 220.

The phrase "passing through the protection film 400" may mean "passing through pores (not shown) of the waterproof film of the protection film 400." When the pores of the waterproof film of the protection film 400 have a diameter less than about 0.1 μm, the gas may have difficulty in passing through the protection film 400. When the pores of the waterproof film of the protection film 400 have a diameter greater than about 10 μm, the impurities may pass through the protection film 400. In some embodiments, the pores of the waterproof film of the protection film 400 may have a diameter ranging from about 0.1 μm to about 10 μm. The protection film 400 may accordingly allow the gas to pass through, but not allow the impurities to pass through. A thickness of the waterproof film of the protection film 400 may be appropriately adjusted to select gas passing through the protection film 400. In some embodiments, the thickness of the waterproof film of the protection film 400 may fall within a range from about 10 μm to about 500 μm. The protection film 400 may thus selectively allow the gas to pass through.

According to example embodiments, the protection film 400 may include a polymer. In some embodiments, the protection film 400 may include a hydrophobic polymer to prevent the cavity 195 from receiving hydrophilic impurities such as moisture. The hydrophobic polymer may include, for example, poly(tetrafluoroethylene)(PTFE). The protection film 400 may be acquired from Goretex Co., but not limited thereto. The protection film 400 may be homogenously formed of the same material.

A connection member 130 may be provided between the package substrate 100 and the lid 300. The connection member 130 may fix the lid 300 to the package substrate 100. The connection member 130 may be interposed between the upper ground pad 115 and the lid 300, thereby being coupled to the upper ground pad 115. The lid 300 may be electrically grounded through the connection member 130 and the upper ground pad 115. The connection member 130 may include a conductive adhesive or a solder material. For example, the conductive adhesive may conductive particles dispersed within an insulating resin. The insulating resin may include an epoxy-based resin, and the conductive particles may include metal. The solder material may include, for example, tin (Sn), lead (Pb), indium (In), or an alloy thereof. When the lid 300 includes a conductive material such as metal, the lid 300 may shield electromagnetic interference (EMI) of the gas sensor package 10. The electromagnetic interference may mean that transceiving functions of electronic devices suffer from disturbance caused by electromagnetic waves emitted or transmitted from other electronic devices. The lid 300 may reduce or prevent operations of the control device 210 and the sensing devices 220 from disturbing, or being disturbed by, operations of other packages. Alternatively, the lid 300 may be electrically disconnected to the upper ground pad 115.

The lid 300, together with the package substrate 100 and connection member 130, may encapsulate the control device 210 and sensing devices 220 and seal the same within cavity 195. With the exception of gas allowed to pass through the protection film 400, the cavity 195 may be hermetically sealed and thus only allow gas to flow in an out of cavity 195 via pores of the protection film 400.

Figure 2A:
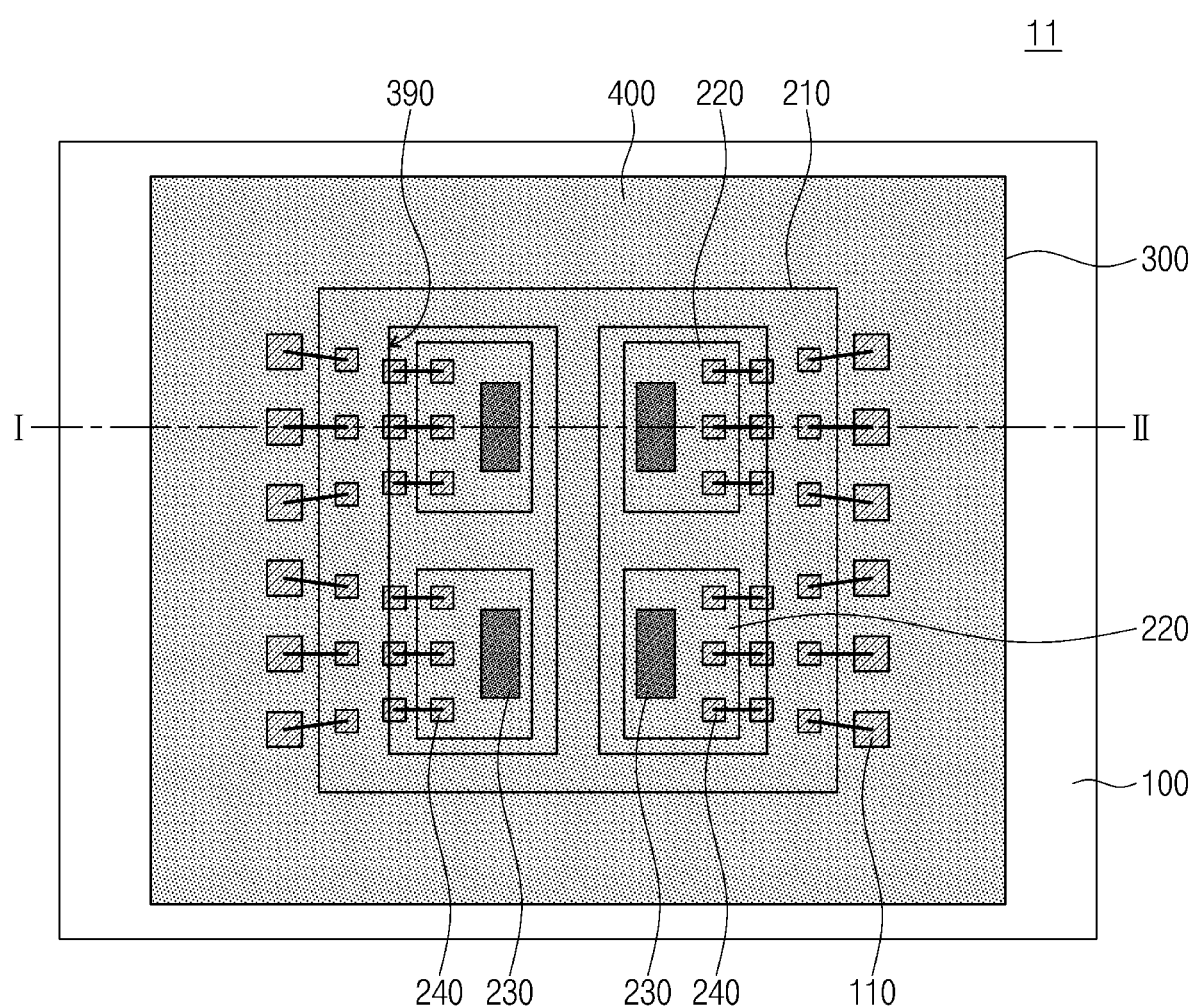
FIG. 2A illustrates a plan view showing a gas sensor package according to exemplary embodiments.
Figure 2B:
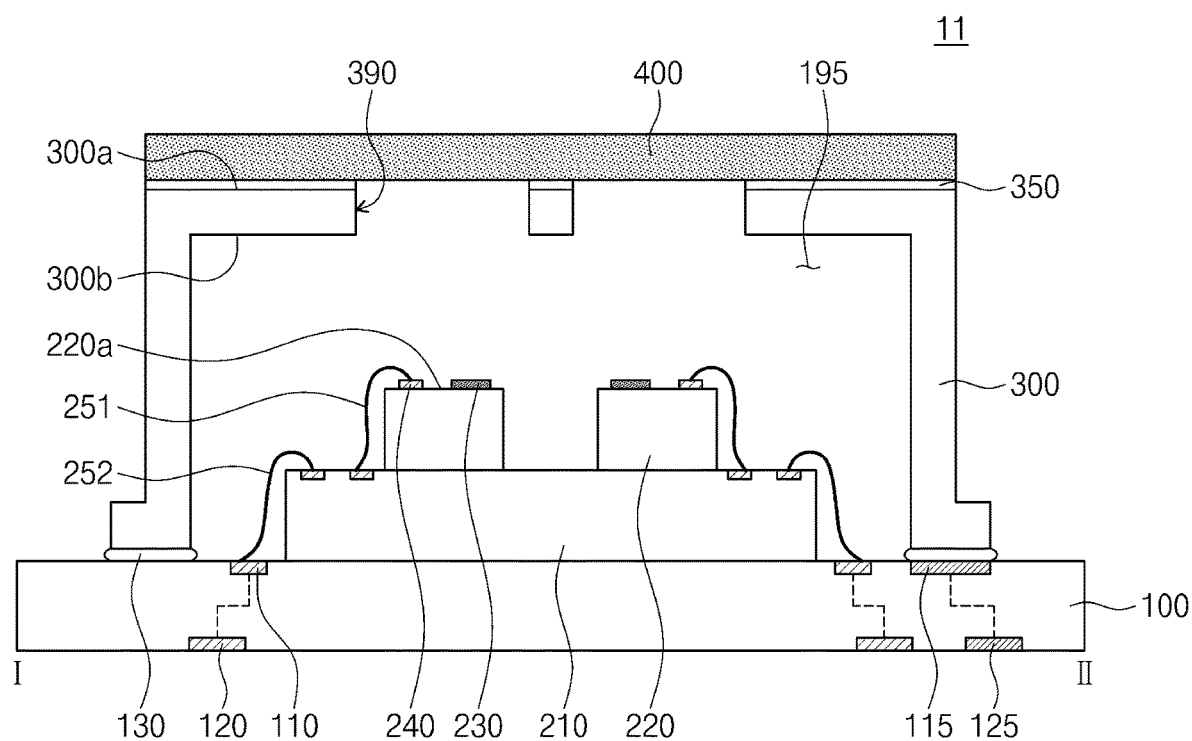
FIG. 2B illustrates a cross-sectional view taken along line I-II of FIG. 2A.

FIG. 2A illustrates a plan view showing a gas sensor package according to exemplary embodiments. FIG. 2B illustrates a cross-sectional view taken along line I-II of FIG. 2A. A description duplicate with the aforementioned will be omitted hereinafter.

Referring to FIGS. 2A and 2B, a gas sensor package 11 may include a package substrate 100, a control device 210, sensing devices 220, a lid 300, and a protection film 400. The package substrate 100, the control device 210, the sensing devices 220, the lid 300, and the protection film 400 may be substantially the same as those discussed above with reference to FIGS. 1A and 1B. In contrast, the protection film 400 may be disposed on a first surface 300a of the lid 300. The protection film 400 may block holes 390. The protection film 400 may overlap the holes 390 when viewed in plan as illustrated in FIG. 2A. The protection film 400 may have a width greater than a sum of widths of the holes 390.

An adhesion film 350 may be interposed between the protection film 400 and the first surface 300a of the lid 300. The protection film 400 may be adhered though the adhesion film 350 to the lid 300. The adhesion film 350 may extend neither into nor onto the holes 390. The adhesion film 350 may seal between the lid 300 and the protection film 400. Therefore, no external impurities may be introduced between the lid 300 and the protection film 400. In this exemplary embodiment, the outer side surfaces of the protection film 400, the lid 300, and the adhesion film 350 may be coplanar as illustrated in FIG. 2B. The adhesion film 350 may include a polymer (e.g., an epoxy-based polymer).

Figure 2C:
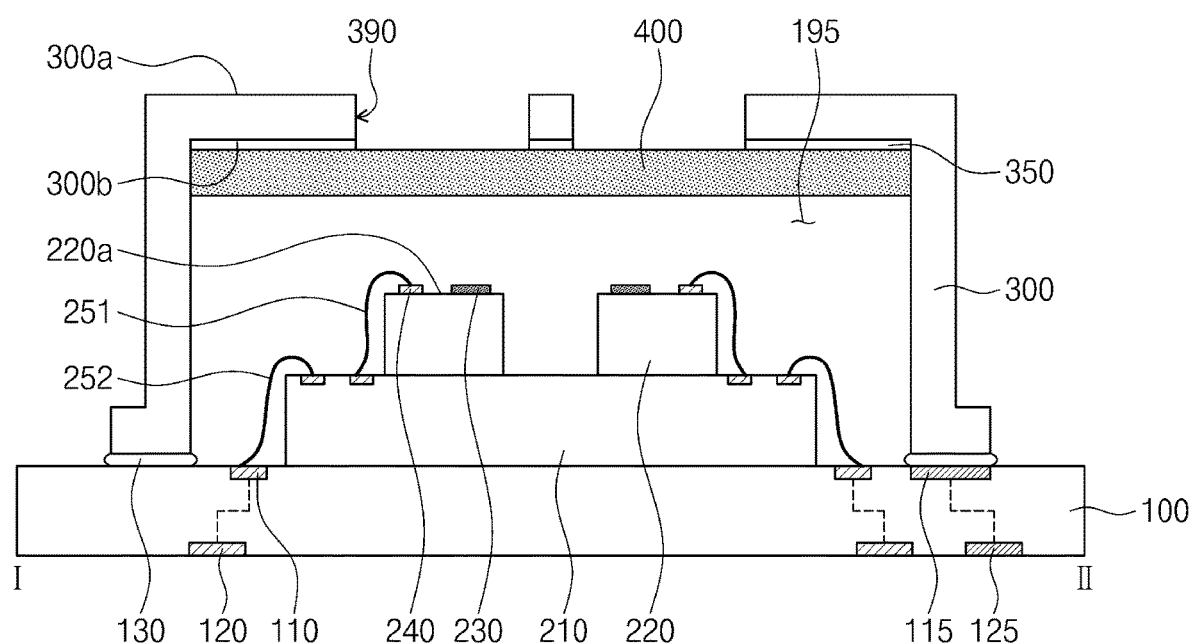
FIG. 2C illustrates a cross-sectional view showing a gas sensor package according to exemplary embodiments.

FIG. 2C illustrates a cross-sectional view taken along line I-II of FIG. 2A, showing a gas sensor package according to exemplary embodiments.

Referring to FIGS. 2A and 2C, a gas sensor package 12 may include a package substrate 100, a control device 210, sensing devices 220, a lid 300, and a protection film 400. The package substrate 100, the control device 210, the sensing devices 220, the lid 300, and the protection film 400 may be substantially the same as those discussed above with reference to FIGS. 1A and 1B. In contrast, the protection film 400 may be disposed on a second surface 300b of the lid 300. The protection film 400 may block holes 390. An adhesion film 350 may be interposed between the protection film 400 and the second surface 300b of the lid 300. The adhesion film 350 may seal between the lid 300 and the protection film 400. In this exemplary embodiment, the outer side surfaces of the protection film 400 and the adhesion film 350 and inner side surfaces of the lid 300 further away from the holes 390 and connected to the connection member 130 may be coplanar as illustrated in FIG. 2C.

Figure 3A:
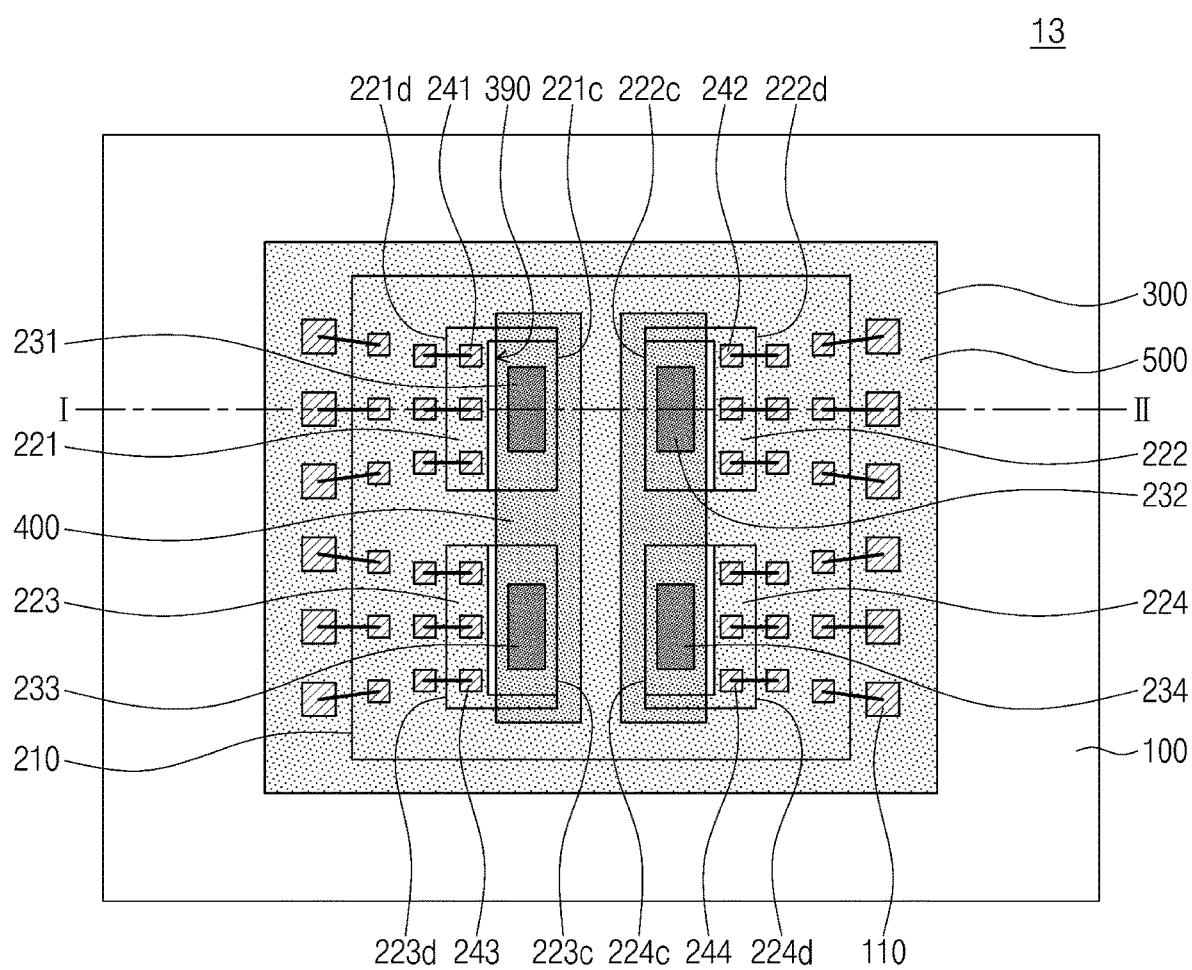
FIG. 3A illustrates a plan view showing a gas sensor package according to exemplary embodiments.
Figure 3B:
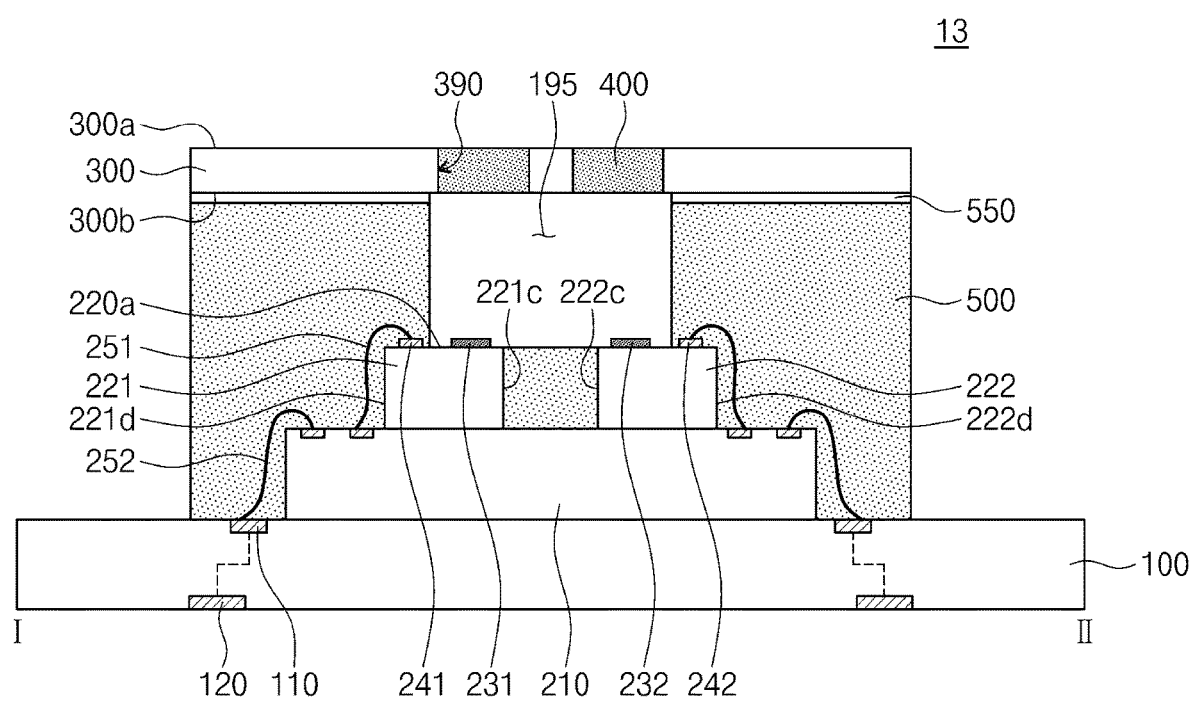
FIG. 3B illustrates a cross-sectional view taken along line I-II of FIG. 3A.

FIG. 3A illustrates a plan view showing a gas sensor package according to exemplary embodiments. FIG. 3B illustrates a cross-sectional view taken along line I-II of FIG. 3A. A description duplicate with the aforementioned will be omitted hereinafter.

Referring to FIGS. 3A and 3B, a gas sensor package 13 may include a package substrate 100, a control device 210, sensing devices 221, 222, 223, and 224, a lid 300, a protection film 400, and a molding layer 500. The package substrate 100, the control device 210, and the protection film 400 may be substantially the same as those discussed above with reference to FIGS. 1A and 1B. For example, the protection film 400 may reside in and block holes 390.

The sensing devices 221 to 224 may include a first sensing device 221, a second sensing device 222, a third sensing device 223, and a fourth sensing device 224. The sensing devices 221 to 224 may be substantially the same as the sensing devices 220 discussed above with reference to FIGS. 1A and 1B. Each of the sensing devices 221 to 224 may have a corresponding one of first sidewalls 221c, 222c, 223c, and 224c and a corresponding one of second sidewalls 221d, 222d, 223d, and 224d facing their counterpart first sidewalls 221c to 224c. Two first sidewalls of neighboring two sensing devices 221 to 224 may face each other. For example, the first sidewall 221c of the first sensing device 221 may face the first sidewall 222c of the second sensing device 222. The first sidewall 223c of the third sensing device 223 may face the first sidewall 224c of the fourth sensing device 224.

The first sensing device 221 may include a first sensing part 231 and a first bonding pad 241. The second sensing device 222 may include a second sensing part 232 and a second bonding pad 242. As illustrated in FIG. 3A, the third sensing device 223 may include a third sensing part 233 and a third bonding pad 243. The fourth sensing device 224 may include a fourth sensing part 234 and a fourth bonding pad 244. The first to fourth sensing parts 231 to 234 may be substantially the same as the sensing parts 230 discussed above with reference to FIGS. 1A and 1B. The first to fourth sensing parts 231 to 234 may include different material compositions from each other. For example, a material composition of the second sensing part 232 may be different from a material composition of the first sensing part 231. Thus, a gas adsorbed to the second sensing part 232 may be of different type from a gas adsorbed to the first sensing part 231. The first to fourth sensing parts 231 to 234 may sense different types gases from each other.

The sensing devices 221 to 224, as illustrated in FIG. 3A, may be configured such that the sensing parts 231 to 234 are disposed closer than their corresponding bonding pads 241 to 244 to their corresponding first sidewalls 221c to 224c. For example, the first sensing part 231 may be closer than the first bonding pad 241 to the first sidewall 221c of the first sensing device 221. The second sensing part 232 may be closer than the second bonding pad 242 to the first sidewall 222c of the second sensing device 222. In such a configuration, when viewed in plan, the first and second sensing parts 231 and 232 may be disposed adjacent to each other. For example, when viewed in plan, the first and second sensing parts 231 and 232 may be disposed between the first bonding pad 241 and the second bonding pad 242. The third sensing part 233 may be closer than the third bonding pad 243 to the first sidewall 223c of the third sensing device 223. The fourth sensing part 234 may be closer than the fourth bonding pad 244 to the first sidewall 224c of the fourth sensing device 224. In such a configuration, when viewed in plan, the third and fourth sensing parts 233 and 234 may be disposed adjacent to each other. When viewed in plan, the first to fourth sensing parts 231 to 234 may be disposed on a central portion of the control device 210. When viewed in plan, the bonding pads 241 to 244 may be disposed closer than the sensing parts 231 to 234 to an edge of the control device 210.

The molding layer 500 may be provided on the package substrate 100, covering the control device 210 and the sidewalls 221c, 221d, 222c, 222d, 223c, 223d, 224c, and 224d of the sensing devices 221 to 224. The molding layer 500 may extend onto a portion of a top surface 220a of each of the sensing devices 221 to 224. The molding layer 500 may cover the first to fourth bonding pads 241 to 244. Since the first to fourth bonding pads 241 to 244 are disposed closer than the sensing parts 231 to 234 to the edge of the control device 210, it may be easy that the molding layer 500 selectively covers the bonding pads 241 to 244. The molding layer 500 may encapsulate and protect the first to fourth bonding pads 241 to 244. For example, the bonding pads 241 to 244 may be free of moisture-induced damage (e.g., corrosion). The molding layer 500 may cover a first bonding wire 251, a second bonding wire 252, and an upper conductive pad 110. The molding layer 500 may encapsulate and protect the first bonding wire 251, the second bonding wire 252, and the upper conductive pad 110.

The molding layer 500 may not cover the sensing parts 231 to 234. The sensing parts 231 to 234 may be exposed to a cavity 195. The sensing parts 231 to 234 may then sense gases within the cavity 195. The cavity 195 may be defined by the sensing devices 221 to 224, the molding layer 500, the lid 300, and the protection film 400. For example, the cavity 195 may be a space surrounded by the sensing devices 221 to 224, the molding layer 500, the lid 300, and the protection film 400. Since the first to fourth sensing parts 231 to 234 are disposed adjacent to each other in a plan view, it may be easy that the cavity 195 is provided on the first to fourth sensing parts 231 to 234.

The lid 300 may be disposed on a top surface of the molding layer 500. The lid 300 may be spaced apart from package substrate 100, and may not be electrically grounded. An adhesion layer 550 may further be interposed between the molding layer 500 and the lid 300. The adhesion layer 550 may include a polymer (e.g., an epoxy-based polymer). The adhesion layer 550 may seal between the molding layer 500 and the protection film 400. Therefore, no external impurities may be introduced between the molding layer 500 and the protection film 400. In this exemplary embodiment, the outer side surfaces of the molding layer 500, the lid 300, and the adhesion layer 550 may be coplanar as illustrated in FIG. 3B.

Differently from that shown, one of the third and fourth sensing devices 223 and 224 may not be provided. For another example, a fifth sensing device may further be disposed on the control device 210.

Figure 3C:
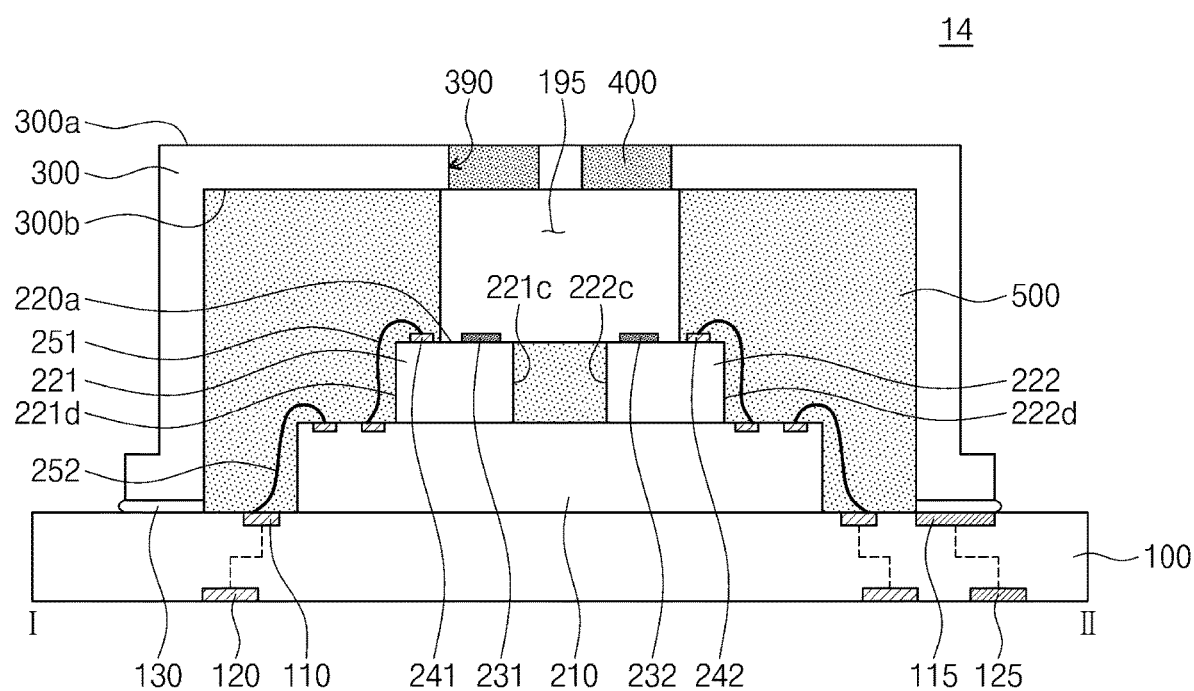
FIG. 3C illustrates a cross-sectional view showing a gas sensor package according to exemplary embodiments.

FIG. 3C illustrates a cross-sectional view taken along line I-II of FIG. 3A, showing a gas sensor package according to exemplary embodiments. A description duplicate with the aforementioned will be omitted hereinafter.

Referring to FIGS. 3A and 3C, a gas sensor package 14 may include a package substrate 100, a control device 210, sensing devices 221, 222, 223, and 224, a lid 300, a protection film 400, and a molding layer 500. The package substrate 100, the control device 210, the sensing devices 221 to 224, the protection film 400, and the molding layer 500 may be substantially the same as those discussed above with reference to FIGS. 3A and 3B. In contrast, the lid 300 may be disposed on a top surface and a sidewall of the molding layer 500. The lid 300 may be substantially the same as that discussed above with reference to FIGS. 1A and 1B. For example, the lid 300 may be rigidly adhered to the package substrate 100 through a connection member 130, as illustrated above in FIG. 1B. The lid 300 may be electrically connected through the connection member 130 to an upper ground pad 115.

Figure 4A:
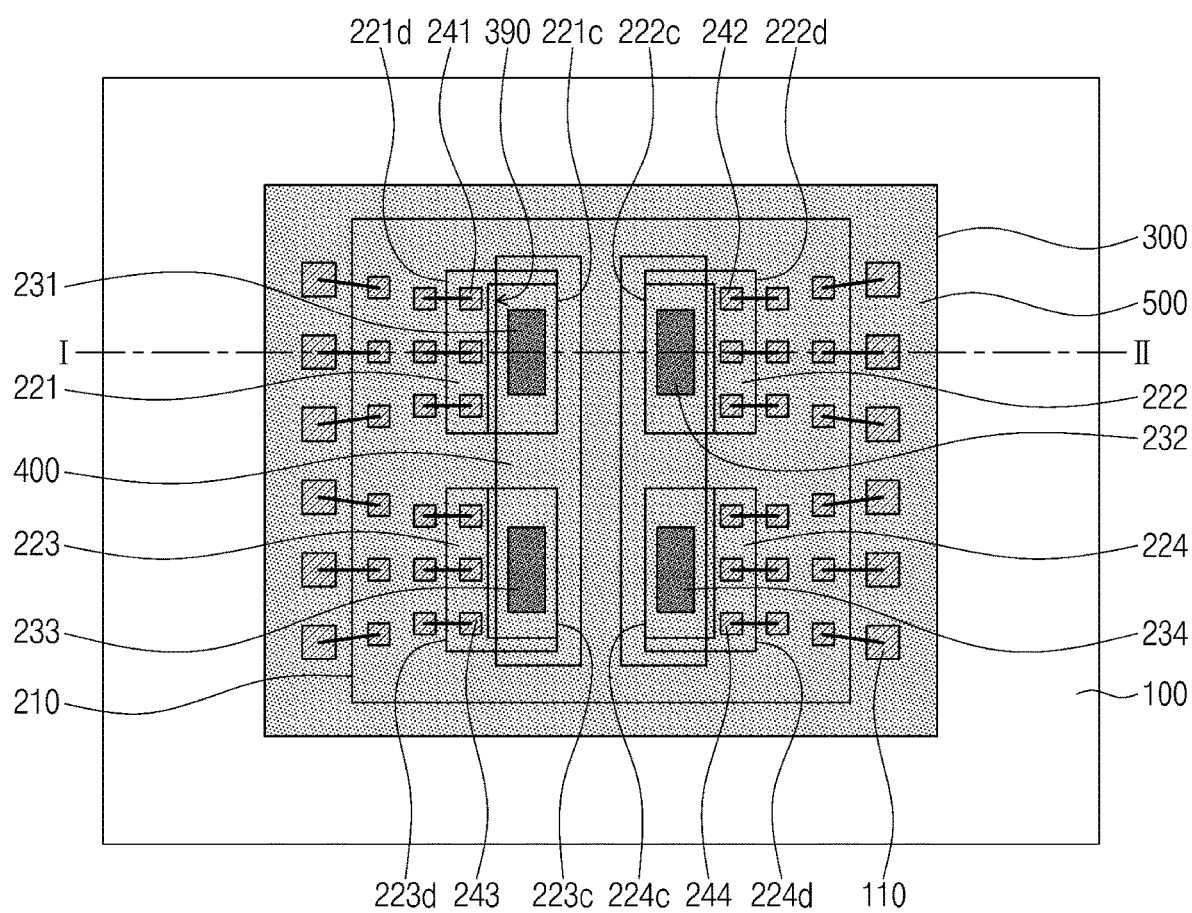
FIG. 4A illustrates a plan view showing a gas sensor package according to exemplary embodiments.
Figure 4B:
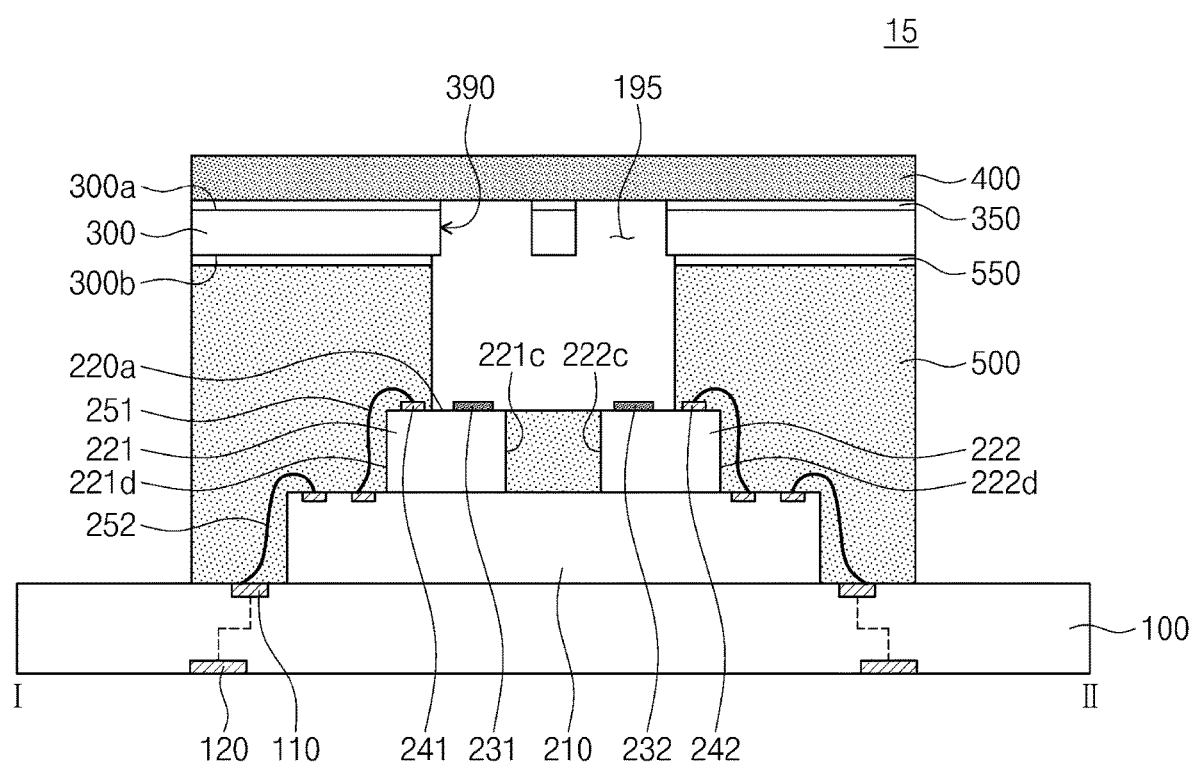
FIG. 4B illustrates a cross-sectional view taken along line I-II of FIG. 4A.

FIG. 4A illustrates a plan view showing a gas sensor package according to exemplary embodiments. FIG. 4B illustrates a cross-sectional view taken along line I-II of FIG. 4A. A description duplicate with the aforementioned will be omitted hereinafter.

Referring to FIGS. 4A and 4B, a gas sensor package 15 may include a package substrate 100, a control device 210, sensing devices 221, 222, 223, and 224, a lid 300, a protection film 400, and a molding layer 500. The package substrate 100 and the control device 210 may be substantially the same as those discussed above with reference to FIGS. 1A and 1B. The sensing devices 221 to 224, the lid 300, and the molding layer 500 may be substantially the same as those discussed above with reference to FIGS. 3A and 3B. The lid 300 may be disposed on a top surface of the molding layer 500. The lid 300 may further extend onto a sidewall of the molding layer 500, as illustrated above in FIG. 3C.

The protection film 400 may be disposed on a first surface 300a of the lid 300 and be blocking holes 390. When viewed in plan, the protection film 400 may overlap the holes 390. The protection film 400 may have a width greater than a sum of widths of the holes 390. The protection film 400 may be flexible or soft. Nevertheless, the protection film 400 may be rigidly fixed through the lid 300.

An adhesion film 350 may be interposed between the lid 300 and the protection film 400. When viewed in plan, the protection film 350 may not overlap the holes 390. The protection film 400 may be adhered though the adhesion film 350 to the lid 300. The adhesion film 350 may seal between the lid 300 and the protection film 400. Therefore, no external impurities may be introduced between the lid 300 and the protection film 400. An adhesion layer 550 may be interposed between the molding layer 500 and the lid 300.

Figure 4C:
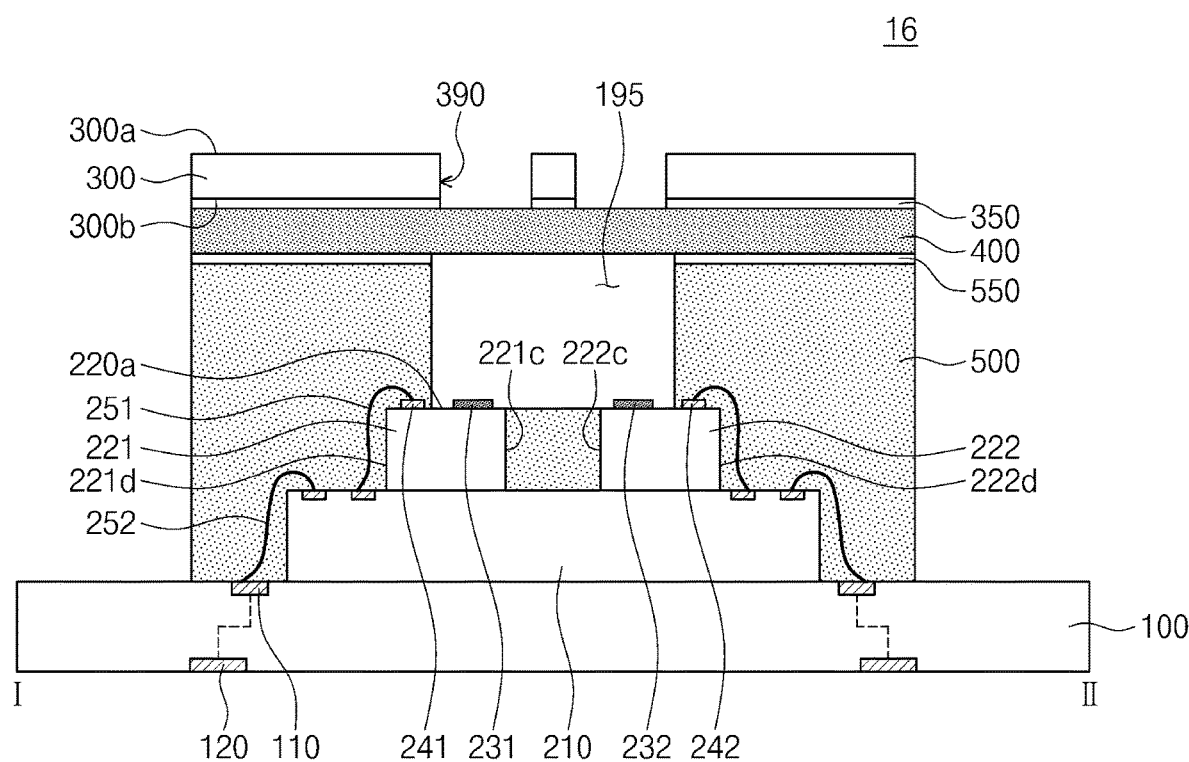
FIG. 4C illustrates a cross-sectional view showing a gas sensor package according to exemplary embodiments.

FIG. 4C illustrates a cross-sectional view taken along line I-II of FIG. 4A, showing a gas sensor package according to exemplary embodiments. A description duplicate with the aforementioned will be omitted hereinafter.

Referring to FIGS. 4A and 4C, a gas sensor package 16 may include a package substrate 100, a control device 210, sensing devices 221, 222, 223, and 224, a lid 300, a protection film 400, and a molding layer 500. The lid 300 may be disposed on a top surface of the molding layer 500. For another example, the lid 300 may further extend onto a sidewall of the molding layer 500, as illustrated above in FIG. 3C.

The protection film 400 may be disposed on a second surface 300b of the lid 300, blocking holes 390. The protection film 400 may be adhered though an adhesion film 350 to the lid 300. The protection film 400 may be more rigidly fixed through the lid 300. When viewed in plan, the protection film 400 may overlap the holes 390. An adhesion layer 550 may be provided between the molding layer 500 and the protection film 400. Thus, according to exemplary embodiments, upper surface of the protection film 400 is in contact with lower surface of the adhesion film 350 and lower surface of the protection film 400 is in contact with upper surface of the adhesion layer 550. According to exemplary embodiments as illustrated in FIGS. 4B and 4C, a side portion of the lid 300 may not extend and contact the upper surface of the package substrate 100. When an element is referred to as "in contact with" another element, there are no intervening elements present at the point of contact.

Figure 5:
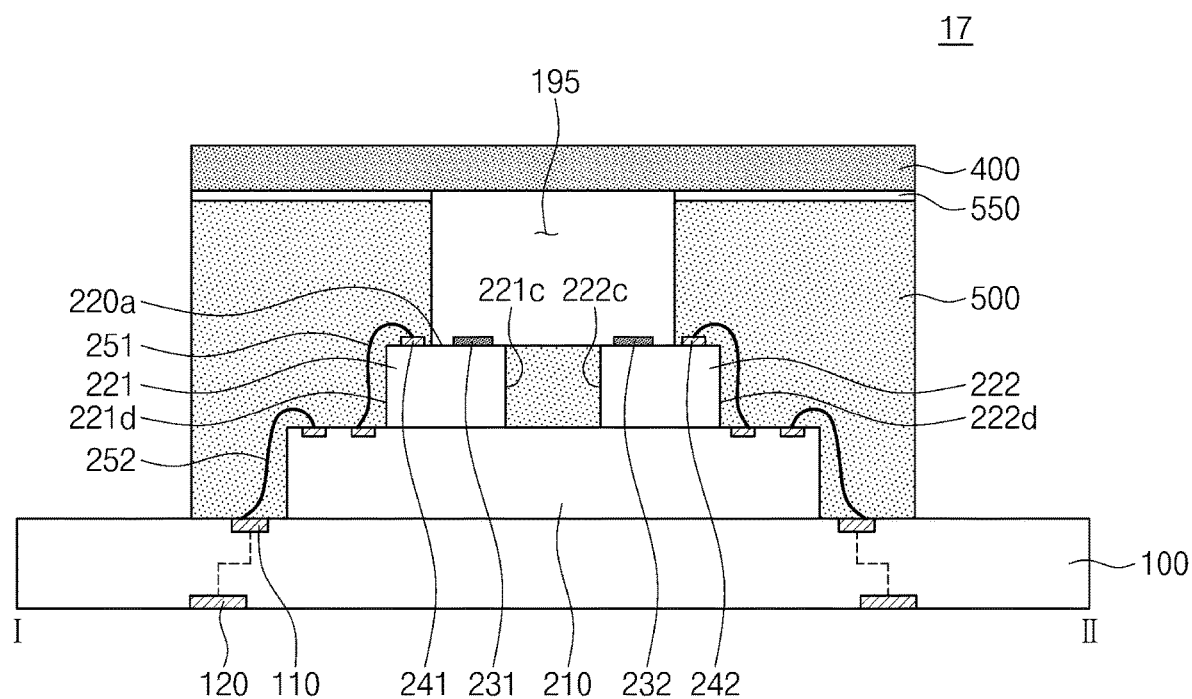
FIG. 5 illustrates a cross-sectional view showing a gas sensor package according to exemplary embodiments.

FIG. 5 illustrates a cross-sectional view showing a gas sensor package according to exemplary embodiments. A description duplicate with the aforementioned will be omitted hereinafter.

Referring to FIG. 5, a gas sensor package 17 may include a package substrate 100, a control device 210, first and second sensing devices 221 and 222, a protection film 400, and a molding layer 500. The package substrate 100, the control device 210, the first and second sensing devices 221 and 222, and the molding layer 500 may be substantially the same as those discussed above with reference to FIGS. 3A and 3B. Although not shown, the control device 210 may further be provided thereon with a third sensing device and a fourth sensing device. In contrast, the lid 300 may not be provided.

The protection film 400 may be provided on the molding layer 500, and spaced apart from a top surface 220a of each of the sensing devices 221 and 222. A cavity 195 may be defined by the sensing devices 221 and 222, the molding layer 500, and the protection film 400. For example, the cavity 195 may be provided between the protection film 400 and the sensing devices 221 and 222. The cavity 195 may expose sensing parts 231 and 232.

An adhesion layer 550 may be interposed between the protection film 400 and the molding layer 500. The protection film 400 may be adhered though the adhesion layer 550 to the molding layer 500. The adhesion layer 550 may not extend between the protection film 400 and the cavity 195.

According to inventive concepts, the protection film may prevent impurities from entering the holes. It therefore may be possible to prevent or reduce the occurrence of sensing noise and damages to the sensing device due to the impurities.

In some embodiments, the sensing device may be provided in plural. The plurality of sensing devices may sense different types of gases from each other. As a result, various kinds of gases may be analyzed.

Although the figures described herein may be referred to using language such as "example embodiments" or "one embodiment," or "certain embodiments," these figures, and their corresponding descriptions are not intended to be mutually exclusive from other figures or descriptions, unless the context so indicates. Therefore, certain aspects from certain figures may be the same as certain features in other figures, and/or certain figures may be different representations or different portions of a particular exemplary embodiment.

This detailed description of inventive concepts should not be construed as limited to the embodiments set forth herein, and it is intended that inventive concepts cover the various combinations, the modifications and variations of this invention without departing from the spirit and scope of inventive concepts. The appended claims should be construed to include other embodiments.

What is claimed is:
1. A gas sensor package, comprising:
a package substrate;
a control device on the package substrate;
a plurality of gas sensors laterally spaced apart from each other on an upper surface of the control device, wherein the plurality of gas sensors comprise a first gas sensor and a second gas sensor spaced apart from each other in a first direction;
a lid on the package substrate and positioned over the plurality of gas sensors, the lid having a hole extending between a first surface and a second surface of the lid, the first surface of the lid facing away the package substrate and the second surface of the lid facing toward the package substrate;
a protection film blocking the hole of the lid;

a first group of a plurality of first conductive pads on an upper surface of the package substrate and electrically connected to the control device through first bonding wires, the plurality of first conductive pads spaced apart from each other in a second direction different from the first direction; and a second group of a plurality of second conductive pads on the upper surface of the package substrate and electrically connected to the control device through second bonding wires, the second group of the plurality of second conductive pads spaced apart from each other in the second direction, wherein, when viewed in plan, the control device is provided between the first group of the plurality of first conductive pads and the second group of the plurality of second conductive pads, wherein the gas sensors are configured to sense different types of gases, wherein each of the gas sensors comprises a sensing part and a group of a plurality of bonding pads provided on a top surface of each of the gas sensors, wherein the control device is disposed between the upper surface of the package substrate and a bottom surface of each of the gas sensors, wherein the control device has a width different from a width of the package substrate and widths of the gas sensors, wherein the sensing part and the group of the plurality of bonding pads of each of the gas sensors are spaced apart from each other in the first direction, wherein, when viewed in plan, the sensing part of the first gas sensor and the sensing part of the second gas sensor are provided between the group of the plurality of bonding pads of the first gas sensor and the group of the plurality of bonding pads of the second gas sensor, and wherein, when viewed in plan, the sensing part of the first gas sensor and the sensing part of the second gas sensor are provided between the first group of the plurality of first conductive pads and the second group of the plurality of second conductive pads.

2. The gas sensor package of claim 1, further comprising a bonding wire coupled to the control device and one of the gas sensors.

3. The gas sensor package of claim 1,
wherein the gas sensors comprise sensing films, and
wherein a sensing film of one of the gas sensors is formed of a material having a different material composition than that of the sensing film of other one of the gas sensors.

4. The gas sensor package of claim 1, further comprising:
a ground pad on the package substrate; and
a connection member between the package substrate and the lid,
wherein the connection member is coupled to the ground pad.

5. The gas sensor package of claim 1,
wherein the protection film includes a waterproof film,
wherein the protection film is provided in the hole,
wherein the waterproof film has a thickness ranging from about 10 μm to about 500 μm in the hole, and
wherein the waterproof film has pores each having a diameter ranging from about 0.1 μm to about 10 μm.

6. The gas sensor package of claim 1,
wherein the protection film is disposed on a surface of the lid, and when viewed in plan, overlaps the hole.

7. The gas sensor package of claim 1,
wherein the control device includes a semiconductor chip.

8. The gas sensor package of claim 1, further comprising a molding layer on the package substrate and partially covering the top surface of each of the gas sensors.

9. The gas sensor package of claim 8,
wherein the plurality of bonding pads of each of the gas sensors are spaced apart from each other in the second direction, and
wherein the molding layer covers the plurality of the bonding pads and exposes the sensing part.

10. The gas sensor package of claim 9,
wherein the first gas sensor and the second gas sensor are adjacent to each other.

11. A gas sensor package, comprising:
a package substrate;
a control device on an upper surface of the package substrate;
a first gas sensor on the control device, the first gas sensor comprising a first sensing part and a first group of a plurality of first bonding pads,
wherein the plurality of first bonding pads are spaced apart from each other in a first direction, and
wherein the first sensing part and the first group of the plurality of first bonding pads are spaced apart from each other in a second direction different from the first direction and are provided on a top surface of the first gas sensor;
a second gas sensor on the package control device, the second gas sensor comprising a second sensing part and a second group of a plurality of second bonding pads,
a first group of a plurality of first conductive pads on the upper surface of the package substrate and electrically connected to the control device through first bonding wires, the plurality of first conductive pads spaced apart from each other in the first direction; and
a second group of a plurality of second conductive pads on the upper surface of the package substrate and electrically connected to the control device through second bonding wires, the second group of the plurality of second conductive pads spaced apart from each other in the first direction,
wherein the plurality of second bonding pads are spaced apart from each other in the first direction, and
wherein the second sensing part and the second group of the plurality of second bonding pads are spaced apart from each other in the second direction and are provided on a top surface of the second gas sensor;
a molding layer on the package substrate, the molding layer covering the first bonding pads and the second bonding pads;
a lid on the molding layer and spaced apart from the first and second gas sensors, the lid including a first hole extending between a first surface of the lid and a second surface of the lid, the first surface of the lid facing away the package substrate and the second surface of the lid facing toward the package substrate; and
a protection film filling the first hole, the protection film being spaced apart from the top surface of the first gas sensor and the top surface of the second gas sensor,
wherein, when viewed in plan, the protection film and the molding layer are spaced apart from each other,
wherein the molding layer exposes the first sensing part and the second sensing part,
wherein, when viewed in plan, the first sensing part of the first gas sensor and the second sensing part of the second gas sensor are spaced apart from each other in the second direction and are provided between the first group of the plurality of first bonding pads of the first gas sensor and the second group of the plurality of second bonding pads of the second gas sensor, and wherein, when viewed in plan, the control device is provided between the first group of the plurality of first conductive pads and the second group of the plurality of second conductive pads.

12. The gas sensor package of claim 11, wherein the first hole overlapping the first sensing part, wherein the first sensing part is positioned closer than the plurality of first bonding pads to a first sidewall of the first gas sensor, in a plan view, and wherein the second sensing part is positioned closer than the plurality of second bonding pads to a first sidewall of the second gas sensor, in a plan view, and wherein the first sidewall of the second gas sensor faces the first sidewall of the first gas sensor.

13. The gas sensor package of claim 11, wherein the protection film comprises a hydrophobic polymer.

14. The gas sensor package of claim 11, wherein the second sensing part is configured to sense a gas whose type is different from that of a gas sensed by the first sensing part.

15. The gas sensor package of claim 11, further comprising:

a third gas sensor on the package substrate, the third gas sensor comprising a third sensing part and a third bonding pad that are laterally spaced apart from each other on a top surface of the third gas sensor; and a fourth gas sensor on the package substrate, the fourth gas sensor comprising a fourth sensing part and a fourth bonding pad that are laterally spaced apart from each other on a top surface of the fourth gas sensor, wherein the molding layer covers the third and fourth bonding pads and exposes the third and fourth sensing parts.

16. The gas sensor package of claim 11, further comprising:

where the lid further includes a second hole extending between the first surface of the lid and the second surface of the lid, and wherein the protection film fills the second hole of the lid.

17. The gas sensor package of claim 16, further comprising a cavity surrounded by the first and second gas sensors, the molding layer, and the protection film.

18. The gas sensor package of claim 16, wherein the first and second gas sensors are stacked on the control device and laterally spaced apart from each other on a top surface of the control device.

* * * * *